United States Patent [19]

McHugh

[11] Patent Number: 4,970,233

[45] Date of Patent: * Nov. 13, 1990

[54] TREATMENT OF ACQUIRED IMMUNODEFICIENCY SYNDROME (AIDS) HTLV-111/LAV INFECTIONS AND ACQUIRED IMMUNODEFICIENCY SYNDROME (AIDS) RELATED COMPLEX (ARC)

[76] Inventor: John E. McHugh, 5139 Balboa Blvd., Ste. 1, Encino, Calif. 91316

[*] Notice: The portion of the term of this patent subsequent to Mar. 17, 1998 has been disclaimed.

[21] Appl. No.: 81,351

[22] Filed: Aug. 4, 1987

[51] Int. Cl.$^5$ ...................... A61K 31/34; A61K 31/19
[52] U.S. Cl. ..................................... 514/470; 514/568
[58] Field of Search ................................ 514/470, 568

[56] References Cited

U.S. PATENT DOCUMENTS 4,256,763  3/1981  McHugh ............................. 514/470
4,588,744  5/1986  McHugh ............................. 514/568

Primary Examiner—Jerome D. Goldberg

[57] ABSTRACT

There is disclosed a method of treating inflammatory viral infections of Acquired Immunodeficiency Syndrome (AIDS) HTLV-111/LAV virus and Acquired Immunodeficiency Syndrome (AIDS) Related Complex (ARC) in humans by stimulating and increasing the rate of Prostaglandin Biosynthesis to levels many times higher than that now occurring naturally thereby enhancing and reconstituting the Immune System, comprising the oral administration of an effective dosage of 3,3-Bis(p-hydroxyphenyl) phthalide (phenolphthalein) by itself or in composition with, or in combination with a Prostaglandin Synthetase inhibitor Aspirin or Indomethacin. Comprising the oral administration of an effective dosage of 3,3-Bis(p-hydroxyphenyl) phthalide (phenolphthalein) by itself or in composition with, or in combination with a Prostaglandins Synthetase inhibitor Aspirin or Indomethacin.

3 Claims, No Drawings

TREATMENT OF ACQUIRED IMMUNODEFICIENCY SYNDROME (AIDS) HTLV-111/LAV INFECTIONS AND ACQUIRED IMMUNODEFICIENCY SYNDROME (AIDS) RELATED COMPLEX (ARC)

BACKGROUND OF THE INVENTION

This invention relates to the discovery that 3,3-Bis(p-hydroxyphenyl)phthalide (phenolphthalein) is an effective treatment for the viral infections Acquired Immunodeficiency Syndrome (AIDS) HTLF-111/LAV and Acquired Immunodeficiency Syndrome (AIDS) Related Complex C) in humans.

Phenolphthalein has long been known as one of a group of primary diphenylmethane cathartics. The cathartic effect of Phenolphthalein was reportedly discovered in 1902 and since that time it has been widely employed in laxative formulas. It is also reported that Phenolphthalein is relatively nontoxic. Goodman & Gillman Pharmacological Basis of Therapeutics (4th Edition 1977) pgs 1021 and 1022. Phenolphthalein is also used as an indicator in the titration of mineral and organic acids and most alkalis Applicant also disclosed methods and uses of phenolphthalein as an antiviral drug in TREATMENT OF HERPES SIMPLEX INFECTIONS AND ACNE, U.S. Pat. No. 4,256,763, filed Sept. 19, 1978 and issued Mar. 17, 1981; and as an antiviral drug for treating mammalian inflammatory viral infections in U.S. Pat. Department No. 4,588,744 filed Jan. 27, 1981 and issued May 13, 1986.

Acquired Immunodeficiency Syndrome (AIDS) HTLV-111/LAV virus is a sexually transmitted terminal disease that ravages the body's immune system and kills by a variety of infections, cancers and brain disorders. It has hit hardest at homosexuals and intravenous drug abusers in the United States, but it is a heterosexual disease in Africa and increasing numbers of cases of heterosexual transmission are being found in the United States and elsewhere.

The AIDS virus was first discovered in May 1983 by Dr. Luc Montagnier of the Pasteur Institute in Paris, France, and by Dr. Robert Gallo of the National Cancer Institute in Bethesda, Md. the following Spring, when he produced the virus in large quantities.

Much evidence suggests that whenever viral infection leads to chronic disease, some sort of breakdown or weakness of the immune system plays a contributing role. The AIDS virus directly attacks helper T cells, or T Lymphocytes as they are known, invading and preventing them from functioning as the initiator of all the immune system response of the human body. With the T cells unable to perform their infection fighting role the AIDS viruses replicate and reproduce themselves a thousand times as fast as any other type virus, spreading with devastating speed to other T cells, destroying them in turn and the immune system of the human body until the patient is beyond recovery. Opportunistic infections attack people when their immune systems are weakened, such as Pneumocystis Carinii pneumonia, a lung infection, Karposi's Sarcoma, a cancer, Candida Albicans, a fungis, Herpes Simplex types 1 & 2, a virus infection, Herpes Zoster, Cytomegalo-Virus and Epstein-Barr viruses.

There are many people infected with the AIDS virus that do not develop the deadly syndrome. They have persistent infections and suffer a mild version of immune-system depression with symptoms that include malaise, weight loss, fevers and swollen lymph nodes. This is the syndrome designated Acquired Immunodeficiency Syndrome (AIDS)-Related Complex or ARC. Much of the time this syndrome developes into full blown AIDS.

Sample studies based on blood tests suggest that millions of Americans are symptomless carriers of the virus. Authorities speculate that 10% of these people without symptoms but with antibodies to the virus, meaning they have been exposed, will develop AIDS within five years.

Progress in the treatment of AIDS has been slow. Some potential antiviral substances have been tested and while they stop or slow replication of the AIDS virus temporarily they Produce debilitating side effects, are not effective cures, and no such cure is in sight. Among these drugs are HPA-23 developed by the Pasteur Institute, and Foscarnet developed in Sweden, Suramin originally used to treat sleeping sickness, Dideoxycytidine, and the first U.S. approved drug for use 3'-Azido-3'-Deoxythymidine "AZT" that while limitedly effective has reportedly caused damage to the marrow of some patient's bones and could have even worse long range effects.

It is an object of the present invention to provide a fast acting, effective treatment of the inflammatory viral infection Acquired Immunodeficiency Syndrome (AIDS) HTLV-111/LAV and Acquired Immunodeficiency Syndrome (AIDS)-Related Complex ARC.

It is a further object of this invention to Provide a fast acting effective treatment that will suppress the AIDS virus HTLV-111/LAV and at the same time rejuvenate, rebuild, and reconstitute the immune system response.

It is a further object of this invention to provide a fast acting, effective treatment of opportunistic infections that attack persons when their immune systems are weakened by AIDS and RC infections such as Pneumocystis Carinii pneumonia, a 1 lung infection, Karposi's Sarcoma, a cancer, Candida Albicans a fungis, Herpes Zoster, HerPes Simplex types 1 and 2, Cytomegalovirus, and Epstein-Barr virus.

The daily maintenance dose for laxative effect of Phenolphthalein and the management thereof is 50 to 100 milligrams in twenty-four hours. Therefore dosage of 200 milligrams or more of phenolphthalein every twelve hours would be prohibitive unless the laxative effect of the drug was suppressed and inhibited. Yellow phenolphthalein commonly used in most laxative products is two to three times stronger as a laxative-cathartic than the pure white Phenolphthalein U.S.P./N.F. and the harsh cathartic effect of the yellow phenolphthalein is difficult to suppress, if possible at all.

It has been discovered by the inventor that the laxative effect of Phenolphthalein can be almost totally suppressed, and practically eliminated by combination with a Prostaglandins Synthetase inhibitor which may be administered one hour before the dosage of the phenolphthalein is given, or contemporaneously therewith, or combined in a composition with phenolphthalein. This would allow the use of high dosages of Phenolphthalein where indicated to effectively use the antiviral Prostaglandin Biosynthesis stimulating properties of the drug.

It would thus be desirable to provide a pharmaceutical composition that suppresses the laxative effect of phenolphthalein at high dosage levels but does not reduce its antiviral Prostaglandin Biosynthesis stimulating activity or enhancement of immunological response.

Indomethacin and Aspirin were found to be two Prostaglandins Synthetase Inhibitors that could be effectively used with Phenolphthalein to accomplish this purpose.

Accordingly it is an object of the present invention to provide novel pharmaceutical compositions containing phenolphthalein and a prostaglandins synthetase inhibitor.

It is also an obJect of the present invention to provide a method and composition of matter for treating the Acquired Immunodeficiency Syndrome (AIDS) and Acquired Immunodeficiency Syndrome (AIDS) Related Complex (ARC) infections by oral administration of the aforesaid pharmaceutical compositions.

Phenolphthalein is a potent stimulant of Prostaglandin Biosynthesis. Prostaglandins function primarily as agents of bodily defense in response to injurious stimulus. Prostaglandins a naturally occurring group of substances represent a diverse family of oxygenated derivatives formed from certain polyunsaturated fatty acids. The biosynthesis of Prostaglandins consists of many steps that involve a variety of different enzymes and cofactors.

It is well established that Prostaglandins are important immunoregulators and their role in immune response is currently being investigated. The stimulation of Prostaglandin Biosynthesis by Phenolphthalein will greatly increase the issue of metabolites to act as local immunoregulators at all physiological and pathological situations in the body. Proliferation of Lymphocyte T Helper cells can be induced by Prostaglandins.

Immune responses are complex often requiring cooperation between several cell types, genetic and other immune-controlling influences, operating at a number of levels, providing an extremely complex regulatory system that is only beginning to be understood.

Prostaglandins are not normally stored in the tissues but are biosynthesized from fatty acids as and when required on injurious stimulus. Prostaglandins are involved in many physiological and pathological situations. They are involved in the protection of renal function against excessive activity of the pressor hormones, remaining dormant until challanged. The lungs are involved in the metabolism of Prostaglandins but little is known about the biological activity of the metabolites that are formed. Prostaglandins have potent effects upon Bronchial and Pulmonary vascular smooth muscle and the lungs have evolved enzyme systems in response to their biological activity.

Prostaglandins are metabolized by tissues to a variety of products in enzymatic reactions, everywhere in the body resulting from injurious stimulus. They are synthesized and released from various regions of the body, including for example the Central Nervous System, the Cerebro Spinal Fluid, Coronary Arteries, all layers of the Heart, the Spleen, the Brain, the Kidneys, the Liver and the Semen, a total body defense system activated instantly on localized pathogenic stimulus. But like Human Interferon the Prostaglandins at their normal synthesized levels of concentration are not strong enough to inhibit the growth of the invading pathogens. What is needed is an excitant to stimulate the rate of Prostaglandin Biosynthesis to levels many times higher than that now occurring naturally. It is believed that Phenolphthalein will provide that needed stimulant.

Prostaglandin Biosynthesis stimulated by the oral administration of effective doses of Phenolphthalein will cause metabolic formulations, in powerful concentrations at high levels of Prostaglandins effective against among other infections, the Acquired Immunodeficiency Syndrome (AIDS)HTLV-111/LAV and Acquired Immunodeficiency Syndrome (AIDS) Related Complex (ARC).

It was found that while the Phenolphthalein laxative effect stimulated by Prostaglandin Biosynthesis activity will be suppressed by ingestion of Aspirin or Indomethacin, Prostaglandin Synthetase inhibitors, for a limited dose related time, the response of the Prostaglandins in all other areas of the body as immunoregulators is not diminished.

It is an object of the present invention to provide a method and composition of matter for treating the Acquired Immunodeficiency Syndrome (AIDS) HTLV TM 111/LAV and Acquired Immunodeficiency Syndrome (AIDS) Related Complex infections by oral administration of Phenolphthalein in effective doses to stimulate and increase the rate of Prostaglandin Synthesis to levels many times higher than that now occurring naturally and thereby enhance and reconstitute the immune system and increase the numbers of Helper-Inducer T Lymphocytes in combatting the infections.

SUMMARY OF THE INVENTION

The novel pharmaceutical compositions and methods of administration of the present invention provide for the treatment of inflammatory viral infections Acquired Immunodeficiency Syndrome (AIDS) HTLV-111/LAV and Acquired Immunodeficiency Syndrome (AIDS) Related Complex RC) by the administration of an effective oral dosage of Phenolphthale in composition with, or in combination with, or taken separately at different prescribed times, with an effective dosage of a Prostaglandin Synthetase inhibitor, Indomethacin or Aspirin to suppress the laxative effect of the Phenolphthalein.

Low dosages of the composition would be given to persons with no symptoms but with circulating antibodies to the HTLV-111 virus meaning they have been exposed. Higher dosages would be administered to persons with full blown Acquired Immunodeficiency Syndrome (AIDS) and or Acquired Immunodeficiency Syndrome (AIDS) Related Complex (ARC) and opportunistic infections Pneumocystis Carinii pneumonia, Herpes Simplex Viruses, Herpes Zoster, Cytomegalovirus, Epstein-Barr virus and Candida Albicans fungis.

Phenolphthalein at high dosage levels effectively provides immediate antiviral Prostaglandin Biosynthesis activity and stimulates fast acting immunological reconstruction with substantial increase in numbers of helper-inducer T cells in early therapy and is virustatic at the high dose levels.

Phenolphthalein is a potent stimulant of Prostaglandin Synthesis a naturally occurring group of substances formed in tissues from polyunsaturated fatty acids in response to injurious stimulus, functioning primarily as agents of bodily defense, and are important imnunoregulators. The factors that determine the rate of Prostaglandin Synthesis are unknown. The synthesis is inhibited by non-steroidal anti-inflammatory drugs such as Indomethacin and Aspirin.

Prostaglandins have potent effects upon bronchial and pulmonary vascular smooth muscle, and the lungs have evolved enzyme systems in response to their biological activity. Prostaglandin levels are elevated when neuronal activity is pathologically enhanced and as a result of inflammatory states and brain damage. These conditions are known to stimulate Prostaglandin synthesis. Prostaglandins are potent pyretic agents. They are found in every principal organ of the human body, the brain, the heart, the lungs the kidneys, the liver, the spleen, the Cerebro Spinal Fluid, the central nervous system, and the semen.

While the mechanism of action of the Prostaglandins is not fully understood, it is well established that they act as immunoregulators at all physiological and pathological situations arising in the body, the result of injurious stimulus. Their main function is in the regulation of Lymphocyte activity, a key element in immune response. (Goodwin & Ceuppens 1983).

Prostaglandin Synthesis is the most important agent of the normal system of bodily defense naturally existing in the human body, triggered to instant response by every injurious stimulus but lacking in levels of concentration to be effective against such pathogens as Acquired Immunodeficiency Syndrome (AIDS) HTLV-111/LAV and Acquired Immunodeficiency Syndrome (AIDS) Related Complex (ARC).

Oral administration of effective doses of Phenolphthalein provide the stimulant needed to trigger Prostaglandin synthesis in powerful enough concentrations at high levels to be effective against the viral infections.

DETAILED DESCRIPTION

The novel pharmaceutical compositions and methods of administration of the present invention provide for the treatment of inflammatory viral infections Acquired Immunodeficiency Syndrome Aids, HTLV-111/LAV and Acquired Immunodeficiency Syndrome (AIDS) Related Complex (ARC) by the administration of an effective oral dosage of phenolphthalein in composition with, or in combination with, or taken separately at different prescribed times with an effective dosage of a Prostaglandin Synthetase inhibitor such as Indomethacin or Aspirin to suppress the laxative effect of the phenolphthalein.

For persons with no symptoms of AIDS or ARC but with circulating antibodies to the HTLV-111/LAV virus meaning they have been exposed, the orally administered dose is preferably about 100 mgs to 150 mgs of white phenolphthalein administered every twelve (12) hours to treat the condition and prevent further development into full blown AIDS infection within five years a probability predicted by leading medical authorities.

One hour before each orally administered dosage of Phenolphthalein, Aspirin should be administered in an amount equivalent to a minimum of six (6) times the amount of the phenolphthalein milligrams given or instead of Aspirin, the drug Indomethacin may be substituted at a concentration equivalent in milligrams to the phenolphthalein dosage given or one half thereof.

For every 100 milligrams of phenolphthalein dosage given orally, six hundred (600) milligrams of Aspirin, two avarage tablets, or instead of Aspirin, Fifty or One Hundred (50-100) milligrams of Indomethacin, should be administered orally ONE (1) HOUR before the phenolphthalein is administered.

The Aspirin and/or Indomethacin act as Prostaglandin Synthetase inhibitors effectively suppressing the laxative effect of the phenolphthalein but not reducing the antiviral efficacy of the drug or its participation in enhancement of immunological response.

While the aforementioned method of the effective administration of an oral dosage of phenolphthalein and a prostaglandin synthetase inhibitor, Aspirin or Indomethacin, for purposes of this invention are the preferred procedures to be followed, the 100 mgs to 150 mgs of white phenolphthalein and the 600 mgs to 900 mgs of Aspirin, or 50 mgs to 100 mgs of Indomethacin, whichever is used, may be formulated as a composition and taken simultaneously with a minimal loss of effectivity in suppression of the laxative effect.

High orally administered dosages of phenolphthalein, for example 200 milligrams to 400 milligrams of white phenolphthalein administered every twelve (12) hours comprise an effective dosage for purposes of the present invention against the viral infections Acquired Immunodeficiency Syndrome (AIDS) HTLV-111/LAV virus and Acquired Immunodeficiency Syndrome (AIDS) Related Complex (ARC) and opportunistic infections Pneumocystis Carinii pneumonia, Herpes Simplex Virus types 1 & 2, Herpes Zoster, Cytomegalovirus, and Candida Albicans.

One hour before oral administration of 200 mgs or 400 mgs of the phenolphthalein dosage, Aspirin should be administered in an amount equivalent to six (6) times the milligram amount of the phenolphthalein to be given, or instead of Aspirin, the drug Indomethacin may be substituted at a concentration equal in number of milligrams to the phenolphthalein dosage to be given, in this instance 200 mgs or 400 mgs. Thus 1200 mgs Aspirin or 200 mgs Indomethacin would be administered one hour before an oral dosage of 200 mgs of phenolphthalein was taken. Higher dosages of the drug phenolphthalein would require use of greater amounts of the Aspirin or Indomethacin used, calculated on the same basic ratios formulated above, to inhibit the stronger laxative effect that would naturally be expected.

The Aspirin and/or Indomethacin act as Prostaglandin Synthetase inhibitors effectively suppressing the laxative effect of the phenolphthalein.

While the aforementioned method of the effective administration of an oral dosage of phenolphthalein and a prostaglandins synthetase inhibitor, Aspirin or Indomethacin, for purposes of this invention are the preferred procedures to be followed, the 200 mgs to 400 mgs of white phenolphthalein, and the 1200 mgs to 2400 mgs of Aspirin, or the 200 mgs to 400 mgs of Indomethacin, may be formulated as a composition and taken simultaneously with minimal loss of effectivity in suppression of laxative effect.

There are two avenues of drug application and use disclosed in the present invention that while seemingly antagonistic and contradictory are in fact physiologically and pathologically compatable in resulting usage. One approach disclosed in the treatment of viral infection is the use of an effective oral dosage of Phenolphthalein in high concentrations with the resulting laxative effect controlled by oral application of a Prostaglandin Synthetase inhibitor, Aspirin or Indomethacin, and the second avenue disclosed in the treatment of viral infection is the stimulation of Prostaglandin Biosynthetase activity to high level elevated concentrations, to enhance this body defense system and its immunoregulatory activity by oral administration of an effective dosage of Phenolphthalein.

There is substantial argument in the literature that Phenolphthalein stimulates Prostaglandin Synthesis and releases PGE$_2$ like material in the gut (Beubler & Juan 1979, Cohen 1982) and that Prostaglandins mediate the cathartic action of Phenolphthalein, but this still remains to be established In-Vivo.

On the administration of a high dosage of phenolphthalein and a Prostaglandin Synthesis inhibitor, Aspirin or Indomethacin, the inhibitor selectively blocks the stimulant effect of the Prostaglandins synthesized, only on the gastrointestinal smooth muscle, effectively preventing the laxative effect of phenolphthalein. The antiviral characteristics of the phenolphthalein are not diminished. The response of the Prostaglandins in body defense mechanisms and immune system reconstitution in all other areas of the body are not inhibited by the action of the Aspirin or Indomethacin on the gastrointestinal smooth muscle. The Prostaglandin Synthetase inhibitors are only effective for approximately eight to twelve hours while Prostaglandins Synthesis is continuously active wherever there is injurious stimulus to the body. Continued stimulation of Prostaglandin Biosynthetase at high levels of concentration may be maintained by orally administered dosages of Phenolphthalein of 50 mgs to 100 mgs every twenty-four (24) hours without the use of an inhibitor, Aspirin or Indomethacin.

While much has been learned about the metabolism of the Prostaglandins little is known about the biological activity of the metabolites that are formed. It is however well established that Prostaglandins are important immunoregulators.

Although it is not completely understood, it is believed that the combination of the metabolites that issue from the cyclooxygenase pathways, the Prostaglandins, stimulated to high level concentrations, and the high dosage Phenolphthalein administrations are more effective than either ingredient alone. It is believed that this synergistic effect has a powerful influence on the inhibition, replication and recurrent attacks of viral infections.

During the past six months the inventor has been contacted by more than two dozen men and women who indicated they were diagnosed as being infected with Acquired Immunodeficiency Syndrome (AIDS) or Acquired Immunodeficiency Syndrome (AIDS) Relate Complex (ARC) either at the San Francisco General Hospital Aids Clinic or at the Los Angeles Aids Clinic at U.C.L.A., all of whom had used phenolphthalein successfully in curing Herpes Genitalis infections in prior years by using a phenolphthalein product marketed as an OTC product licensed under inventor's earlier patent.

They reported significant improvement in their AIDS and ARC conditions after using high dosages of phenolphthalein treatment to cure their present Herpes infections which in some of the reporting patients were ulcerating infections of the genitals that had raged for weeks. Others reported that they had recovered from Pneumocystis Carinii pneumonia, localized Herpes Zoster, Cytomegalovirus, Epstein-Barr virus and even Candida Albicans after the high dosage phenolphthalein treatment.

Still others of this voluntary informal reporting group of AIDS victims, after using the high dosage phenolphthalein Herpes Genitalis cure successfully, claim improved appetite, and energy, weight increase, improved ability to exercise, loss of headaches and fever with improved sense of well being. Unconfirmed reports of increased numbers of circulating helper-inducer T Lymphocytes and no detectable virus in some of those reporting suggested effectivity of the high dosage phenolphthalein dosages they had taken.

None of the persons reporting noticed any side effects except for some temporary laxative aggrivation easily tollerated.

High oral dosages of 100 milligrams to 400 milligrams, administered every twelve (12) hours, of white phenolphthalein in composition with Aspirin and Indomethacin have been administered to victims of Acquired Immunodeficiency Syndrome (AIDS) HTLV-111/LAV and Acquired Immunodeficiency Syndrome (AIDS) Related Complex ARC with dramatic overall improvement in some instances in as little as five days.

While specific formulations have been given above, it is n intended that they limit the scope of the invention.

The invention is limited only by the scope of the appended claims set forth below.

What is claimed is:

1. The method of treating inflammatory viral infections of Acquired Immunodeficiency Syndrome (AIDS)HTLV-111/LAV virus and Acquired Immunodeficiency Syndrome (AIDS) Related Complex (ARC) in humans comprising the oral administration of an effective antiviral dosage of 3,3-Bis(p-hydroxyphenyl)phthalide, to a person afflicted with at least one of said conditions.

2. The method of claim 1, wherein said dosage comprises from about 100 to 150 milligrams of 3,3-Bis(p-hydroxyphenyl) phthalide.

3. The method of claim 1, wherein said dosage comprises from about 200 to 400 milligrams of 3,3-Bis(p-hydroxyphenyl) phthalide.

* * * * *